United States Patent
Iaccino et al.

(10) Patent No.: US 7,659,437 B2
(45) Date of Patent: Feb. 9, 2010

(54) PROCESS FOR METHANE CONVERSION

(75) Inventors: Larry L. Iaccino, Seabrook, TX (US);
Elizabeth L. Stavens, Seabrook, TX (US); Neeraj Sangar, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 288 days.

(21) Appl. No.: 11/729,559

(22) Filed: Mar. 29, 2007

(65) Prior Publication Data

US 2007/0249879 A1 Oct. 25, 2007

Related U.S. Application Data

(60) Provisional application No. 60/794,058, filed on Apr. 21, 2006.

(51) Int. Cl.
*C07C 2/52* (2006.01)
(52) U.S. Cl. .................. 585/412; 585/400; 585/407; 585/417; 585/418; 585/419; 585/420
(58) Field of Classification Search ......... 585/407–420, 585/400
See application file for complete search history.

(56) References Cited

U.S. PATENT DOCUMENTS

| | | | | |
|---|---|---|---|---|
| 2,809,922 | A * | 10/1957 | Berg et al. ............... 208/64 |
| 3,907,511 | A * | 9/1975 | Forbes et al. ............ 422/191 |
| 4,727,206 | A | 2/1988 | Clayson et al. |
| 5,026,937 | A | 6/1991 | Bricker |
| 5,336,825 | A | 8/1994 | Choudhary et al. |
| 6,239,057 | B1 | 5/2001 | Ichikawa et al. |
| 6,426,442 | B1 | 7/2002 | Ichikawa et al. |
| 2003/0083535 | A1 | 5/2003 | Wright et al. |

OTHER PUBLICATIONS

Mu, Z. et al. (2003). Chemical Engineering and Processing, 42, 409-417.*
Wang, D. et al. (1997). Journal of Catalysis, 169, 347-358.*
Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

* cited by examiner

*Primary Examiner*—Robert J Hill, Jr.
*Assistant Examiner*—Brian McCaig
(74) *Attorney, Agent, or Firm*—Andrew B. Griffis

(57) ABSTRACT

A process for converting methane to higher hydrocarbon(s) including aromatic hydrocarbon(s) comprises providing a hydrocarbon feedstock containing methane and a catalytic particulate material to a reactor system having at least first and second reaction zones connected in series. Each of the reaction zones is operated under reaction conditions sufficient to convert at least a portion of the methane to said higher hydrocarbon(s) and is maintained in a moving bed fashion, with the bulk of the catalytic particulate material being moved from the first reaction zone to the second reaction zone and with the bulk of the hydrocarbon feedstock being moved from the second reaction zone to the first reaction zone.

50 Claims, 1 Drawing Sheet

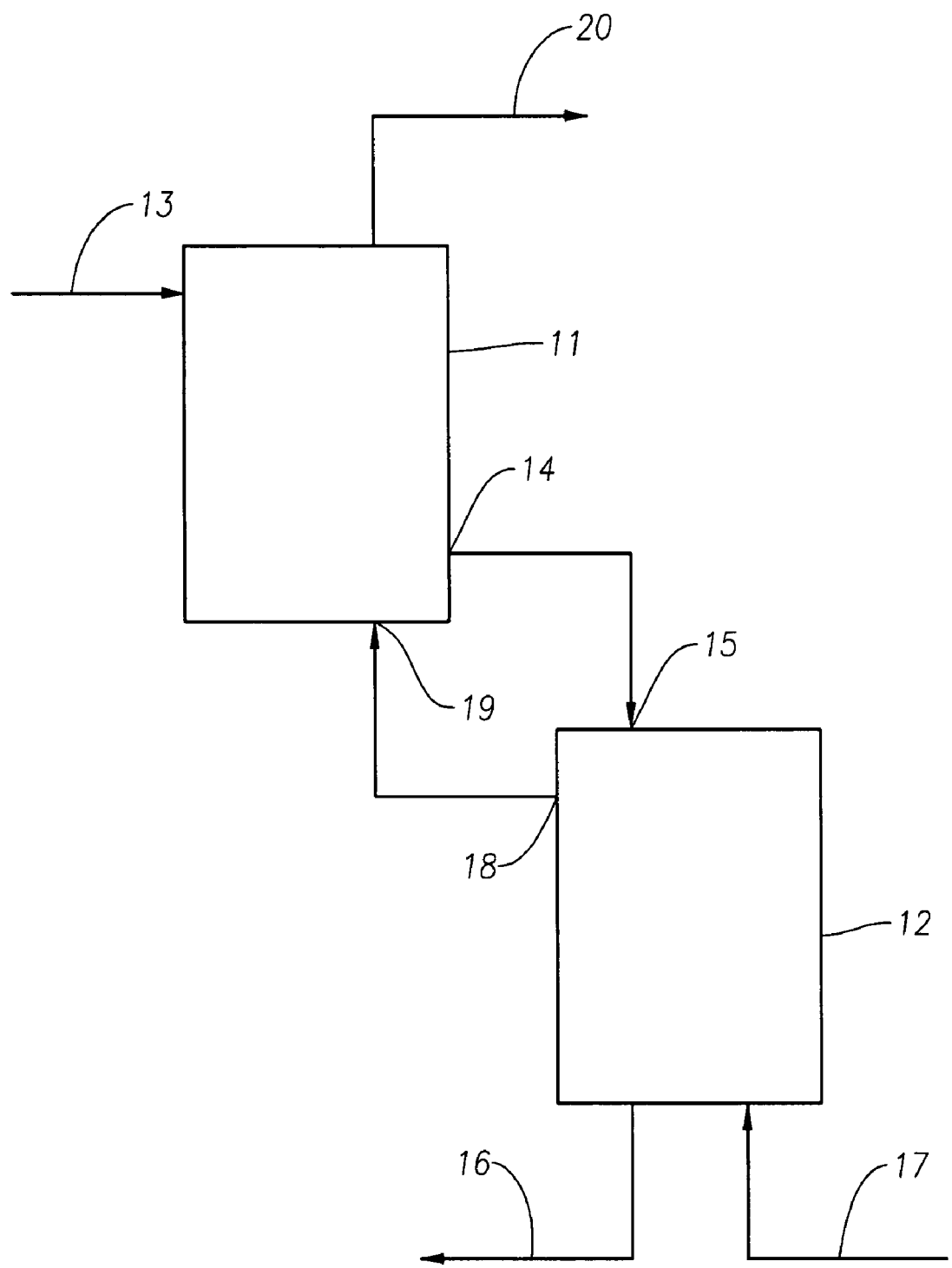

PROCESS FOR METHANE CONVERSION

CROSS REFERENCE TO RELATED APPLICATIONS

This application claims the benefit of Provisional Application No. 60/794,058 filed Apr. 21, 2006, the disclosures of which are incorporated by reference in their entireties.

FIELD

This disclosure relates to a process for methane conversion. In particular, this disclosure relates to a process for natural gas conversion.

BACKGROUND

Aromatic hydrocarbon(s), particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbon(s).

One possible alternative source of aromatic hydrocarbon(s) is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbon(s), such as aromatics, is an attractive method of upgrading natural gas, providing the attendant technical difficulties can be overcome.

A large majority of the processes currently proposed for converting methane to liquid hydrocarbon(s) involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbon(s). One such process involves catalytic oxidative coupling of methane to olefins followed by the catalytic conversion of the olefins to liquid hydrocarbon(s), including aromatic hydrocarbon(s). For example, U.S. Pat. No. 5,336,825 discloses a two-step process for the oxidative conversion of methane to gasoline range hydrocarbon(s) comprising aromatic hydrocarbon(s). In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbon(s) over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbon(s), particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C. Frequently, the catalytically active species of the metal is the zero valent elemental form or a carbide or oxycarbide.

For example, U.S. Pat. No. 4,727,206 discloses a process for producing liquids rich in aromatic hydrocarbon(s) by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPa-a) and a gas hourly space velocity of 400 to 7,500 $hr^{-1}$.

Moreover, U.S. Pat. Nos. 6,239,057 and 6,426,442 disclose a process for producing higher carbon number hydrocarbon(s), e.g., benzene, from low carbon number hydrocarbon(s), such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

WO 03/000826 and U.S. Patent Application Publication No 2003/0083535 disclose a system and method for circulating catalyst between a reactor system and a regenerator system. A circulating catalyst system includes a reactor system, a regenerator system, and a distribution unit. The reactor system and regenerator system are adapted to exchange catalyst. The reactor system preferably includes a fluidized bed riser reactor and the regeneration system preferably includes a regeneration zone adapted for the contact of catalyst with a regeneration gas. The system and method are adapted so that more than one regeneration gas may contact catalyst. The distribution unit is adapted to control the percentage of catalyst contacting each regeneration gas. Thus, the distribution unit is adapted to select the percentage so as to maintain the reactor system and regeneration system under a heat balance regime. Heat is preferably transferred from the regenerator system to the reactor system by an exchange of catalyst.

However, the successful application of reductive coupling to produce higher hydrocarbons, e.g., aromatic compounds, on a commercial scale requires the solution of a number of serious technical challenges. Examples of technical challenges are:

(a) the process is endothermic which requires high energy input;

(b) the process is thermodynamically limited, which requires high temperature operation to achieve high conversion;

(c) the process requires significant amount of make-up heat to compensate the energy requirement of the endothermic reaction and to maintain the high temperature required for high conversion;

(d) the process requires effective heat transfer and effective contact of light hydrocarbon(s) with the catalyst are required to achieve high conversion of methane;

(e) the process generates coke and/or catalyst coking at high temperature;

(f) the process may use feedstocks containing $C_{2+}$ hydrocarbons in addition to methane, which feedstocks may increase coking of the catalyst used in the process; and (g) to reduce problems related to catalyst attrition, it is desirable to minimize the circulation rate and other mechanical stresses on the catalyst.

Accordingly, there is a need to develop a process for converting methane to higher hydrocarbon(s), which provides high efficiency for heat transfer, adequate hydrocarbon/catalyst contacting, improved process conditions to maximize selectivity to desired higher hydrocarbons, e.g., aromatic compound(s), while minimizing coke formation, and minimizing of required catalyst circulation rates.

SUMMARY

In one aspect, the present disclosure resides in a process for converting methane to higher hydrocarbon(s) including aromatic hydrocarbon(s) in a reactor system comprising at least first and second reaction zones connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone;

(d) maintaining said reaction zones in a moving bed fashion; and (e) operating each of said reaction zones under reaction conditions sufficient to convert at least a portion of said methane to a first effluent having said higher hydrocarbon(s).

Additionally, the process further comprises:

(f) removing at least a portion of said catalytic particulate material from said reaction zones; and (g) regenerating at least a portion of the removed catalytic particulate material under regenerating conditions.

Conveniently, the process further comprises:

(h) recycling at least a portion of the regenerated catalytic particulate material to said reaction zones.

In one embodiment, the process further comprises:

(f) removing at least a portion of said catalytic particulate material from said reaction zones; and (g) heating at least a portion of the removed catalytic particulate material to a temperature at least 825° C.

Conveniently, the process further comprises:

(h) recycling at least a portion of the heated catalytic particulate material to said reaction zones.

In a further aspect, the invention resides in a process for converting methane to higher hydrocarbon(s) including aromatic hydrocarbon(s) in a reactor system comprising at least first and second reaction zones connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone;

(d) maintaining said reaction zones in a moving bed fashion;

(e) maintaining said reaction zones with a superficial gas velocity within a range from a minimum fluidization velocity ($U_{mf}$) to a velocity required for maintaining a solid bed void fraction below 95 vol. %;

(f) operating each of said reaction zones under reaction conditions sufficient to convert at least a portion of said methane to a first effluent having said higher hydrocarbon(s);

(g) removing at least a portion of said catalytic particulate material from said reaction zone(s);

(h) regenerating at least a portion of the removed catalytic particulate material under regenerating conditions;

(i) heating at least a portion of the removed catalytic particulate material and/or at least a portion of the regenerated catalytic particulate material to a temperature at least 825° C.; and (j) recycling at least a portion of the heated catalytic particulate material to said reaction zones.

Conveniently said regenerating conditions include a temperature from about 400° C. to about 750° C., such as from about 550° C. to about 650° C.

Conveniently said regenerating conditions comprise a regeneration gas comprising oxygen. Conveniently said regenerating gas further contains carbon dioxide and/or nitrogen such that the oxygen concentration of said regenerating gas is from about 2 wt. % to about 10 wt. %.

In another aspect, this disclosure resides in a process for manufacturing aromatic hydrocarbon(s) from methane in a reactor system comprising at least first and second reaction zones connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone;

(d) maintaining said reaction zones with a superficial gas velocity within a range from a minimum fluidization velocity ($U_{mf}$) to a velocity required for maintaining a solid bed void fraction below 95 vol. %;

(e) operating each said reaction zone under reaction conditions sufficient to convert at least a portion of said methane to a first effluent having said aromatic hydrocarbon(s); and (f) recovering said aromatic hydrocarbon(s).

Generally the reaction conditions of each reaction zone are sufficient to convert at least 5 wt. % of said methane to higher hydrocarbon(s) across the combined reaction zones. In one embodiment, the reaction conditions of each reaction zone are sufficient to convert at least 5 wt. % of said methane to aromatic hydrocarbon(s) across the combined reaction zones.

In another embodiment, the aromatic hydrocarbon(s) includes benzene.

Conveniently, the process further comprises at least one additional reaction zone.

Conveniently, the process further comprises separating unreacted methane from said higher hydrocarbon(s) and recycling said unreacted methane to said reaction zones.

Conveniently, said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent. Optionally, the process comprises recycling said second effluent to step (a).

Conveniently, said catalytic particulate material moves downwardly in said reaction zone(s) and said hydrocarbon feedstock moves upwardly in said reaction zone(s).

Conveniently, said reaction zones are operated at a superficial gas velocity of at least 1.01 times of the minimum fluidization velocity ($U_{mf}$).

Conveniently, said reaction zones are operated at a superficial gas velocity of less than the velocity required for maintaining a solid bed void fraction below 95 vol. %.

Conveniently, the step (a) further comprises supplying to said reactor system a non-catalytic particulate material.

Conveniently, the mass ratio of the total flowrate of said particulate material (catalytic particulate material plus any non-catalytic particulate material) to the flowrate of said hydrocarbon feedstock is from about 1:1 to about 100:1, such as from about 5:1 to about 25:1.

Conveniently, said reactor zones are contained within one or more cold wall reactors.

In one aspect of the abovementioned embodiments, said reaction conditions in each reaction zone are non-oxidizing conditions.

In another aspect of the abovementioned embodiments, the reaction conditions in each reaction zone include a temperature of about 400° C. to about 1200° C., a pressure of about 1 kPa-a to about 1000 kPa-a, and a weight hourly space velocity of about 0.01 hr$^{-1}$ to about 1000 hr$^{-1}$.

In one aspect of the abovementioned embodiments, said catalytic particulate material is a dehydrocyclization catalyst. In one embodiment, said catalytic particulate material comprises a metal or compound thereof on an inorganic support.

In one embodiment, said catalytic particulate material comprises at least one of molybdenum, tungsten, rhenium, a molybdenum compound, a tungsten compound, a zinc compound, and a rhenium compound on ZSM-5, silica or an aluminum oxide.

In one embodiment, said catalytic particulate material enters said second reaction zone at a temperature of about 800° C. to about 1200° C. and exits said second reaction zone at a temperature of about 600° C. to about 800° C. before entering said first reaction zone. Conveniently, the sum of the temperature difference of said catalytic particulate material across said first reaction zone and the temperature difference of said catalytic particulate material across said second reaction zone is at least 100° C.

Conveniently, said hydrocarbon feedstock further comprises at least one of $CO_2$, $CO$, $H_2$, $H_2O$, or $C_2$+ hydrocarbon(s).

In other embodiments of this disclosure, at least a portion of said higher hydrocarbon(s), such as benzene and/or aromatic hydrocarbon(s), is reacted with hydrogen and/or an alkylating agent to produce a derivative of the higher hydrocarbon(s).

These and other facets of the present disclosure shall become apparent from the following detailed description, FIGURE, and appended claims.

BRIEF DESCRIPTION OF THE DRAWINGS

FIG. 1 is a diagram of a process for converting methane to higher hydrocarbon(s) according to one embodiment of the invention.

DETAILED DESCRIPTION OF THE EMBODIMENTS

Definitions

All patents, patent applications, test procedures, priority documents, articles, publications, manuals, and other documents cited herein are fully incorporated by reference to the extent such disclosure is not inconsistent with the present disclosure and for all jurisdictions in which such incorporation is permitted.

When numerical lower limits and numerical upper limits are listed herein, ranges from any lower limit to any upper limit are contemplated.

As used in this specification, the term "framework type" is used in the sense described in, for example, the "Atlas of Zeolite Framework Types," 2001.

As used herein the term "higher hydrocarbon(s)" means hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene.

As used herein the term "aromatic hydrocarbon(s)" means molecule(s) containing one or more aromatic ring(s). Examples of aromatic hydrocarbons are benzene, toluene, ethylbenzene, xylenes (para-xylene, meta-xylene, and ortho-xylene), naphthalene, and methyl naphthalene.

As used herein the term "moving bed" means a zone or vessel wherein particulates contact with gas flows such that the superficial gas velocity (U) is below the velocity required for dilute-phase pneumatic conveying of solid particles in order to maintain a solids bed with void fraction below about 95 vol. % ($U_{95\%}$), optionally below about 85 vol. % ($U_{85\%}$). A moving-bed reactor may operate under several flow regimes including:

(a) settling- or moving packed-bed regime, wherein the superficial gas velocity is less than the minimum fluidization velocity ($U_{mf}$), $U<U_{mf}$;

(b) bubbling regime, wherein the superficial gas velocity is more than the minimum fluidization velocity ($U_{mf}$) and less than the minimum bubbling velocity ($U_{mb}$), $U_{mf}<U<U_{mb}$;

(c) slugging regime, wherein the superficial gas velocity is more than the minimum bubbling velocity ($U_{mb}$) and less than the minimum bubbling velocity ($U_c$), $U_{mb}<U<U_c$;

(d) transition to and turbulent fluidization regime, wherein the superficial gas velocity is more than the minimum velocity ($U_c$) and less than the minimum transport velocity ($U_{tr}$), $U_c<U<U_{tr}$; and (e) fast-fluidization regime, wherein the superficial gas velocity is more than the minimum transport velocity ($U_{tr}$), $U>U_{tr}$.

These different flow regimes have been described in, for example, Chapter 3 of "Fluidization Engineering," D. Kunii and O. Levenspiel, 2$^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "settling bed" means a zone or vessel wherein particulates contact with gas flows such that the superficial gas velocity (U) is below the minimum velocity required to fluidize the solid particles, the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Chapter 3 of "Fluidization Engineering," D. Kunii and O. Levenspiel, $2^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "fluidizing bed" means a zone or vessel wherein particulates contact with gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below about 95%.

As used herein the term "cascade moving beds" means a series arrangement of individual moving beds as the particulates or gas cascades from one moving bed to another.

As used herein the term "cascade fluidizing beds" means a series arrangement of individual fluidizing beds such that there can be a gradient in gas and/or solid property (such as, temperature, gas or particulates composition, pressure etc.) as the particulates or gas cascades from one fluidizing bed to another.

As used herein the term "riser" means a zone or vessel (such as, vertical cylindrical pipe) used for net upwards transport of particulates in fast-fluidization or pneumatic conveying fluidization regimes. Fast fluidization and pneumatic conveying fluidization regimes are characterized by superficial gas velocities (U) greater than the minimum transport velocity ($U_{tr}$). Fast fluidization and pneumatic conveying fluidization regimes are described in, for example, Chapter 3 of "Fluidization Engineering," D. Kunii and O. Levenspiel, $2^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "inverse temperature profile" means that a reactor system having a hydrocarbon gas inlet temperature lower than the hydrocarbon gas outlet temperature—that is the inverse of the temperature profile naturally achieved for an endothermic reaction.

As used herein the term "catalytic particulate material" means a refractory material that causes an increase in the reaction rate of the feed to the desired products at the process conditions. The catalytic particulates material may form particulates without binder or be bound by an inorganic binder such as clay, silica, alumina, zirconia, or other metal oxide, to maintain the physical integrity of the particles. Preferably the particles are of a substantially spherical shape. The particles may contain additional components to provide useful functions by adjusting the thermal conductivity, the density, the heat capacity, and/or the attrition resistance of the catalytic particulate material to secure a desired catalyst performance.

As used herein the term "non-catalytic particulate material" means a particulate material which is not a catalytic particulate material. The non-catalytic particulate material may comprise a refractory inorganic material that does not cause an increase in the reaction rate of the feed to the desired products at the process conditions. The non-catalytic particulate material may be used as a material to transport energy (heat) into the system and/or to fill space as required providing the required hydrodynamic environment. The non-catalytic particulate material may form particulates without binder or be bound by an inorganic binder such as clay, silica, alumina, zirconia, or other metal oxide may be used to help maintain the physical integrity of the particles. Preferably the particles are of a substantially spherical shape.

As used herein the term "cold wall reactor" or "cold wall vessel" means a reactor or a vessel constructed with one or more layers of insulating material between the catalyst of the process and the metallic shell which acts as a pressure containment for the process; whereby a temperature gradient occurs across the insulating material so that the metallic shell is at a substantially lower temperature, such as more than 50° C., for example more than 100° C., such as more than 300° C., and optionally more than 600° C., than the temperature of the contained material.

As used herein the term "non-oxidizing conditions" means conditions wherein oxidizing agents (such as, $O_2$, $NO_x$ and metal oxides which can release oxygen to oxidize methane to $CO_x$) are present at less than 5%, such as at less then 1%, and typcally at less than 0.1%, of the amount required for stoichiometric oxidation of the methane in the feed.

By "supplemental source of fuel" is meant that the source fuel is physically separate from the catalyst and hence is not, for example, coke generated on the catalyst as a by-product of the dehydrocyclization reaction.

As used herein the term "carburizing gas" means any gas that, under the conditions in a catalyst treatment zone, can convert at least a portion of the catalytic metal(s) in the catalytic particulate material from an oxidized state to an elemental form, to a carbidic species, or to a less oxidized form. The carburizing gas can also partly coke active catalytic sites of the catalyst. Such active catalytic sites comprise catalytic metal and/or other active sites capable of catalyzing the desired reaction. The carburizing gas may also deposit a quantity of carbon and/or hydrocarbon species on the catalytic particulate material. Such carbon and/or hydrocarbon species may be intermediates to the formation of the desired higher hydrocarbon(s), e.g., aromatic compound(s). The carburizing gas may comprise hydrocarbons, $H_2$, CO, $CO_2$, and any combination thereof, such that the carburizing gas contains a source of both the element carbon and the element hydrogen.

Introduction

The present disclosure provides a process for producing higher hydrocarbon(s), e.g., aromatic compound(s), by contacting a feedstock containing methane, typically together with $H_2$, CO and/or $CO_2$, with a particulate dehydrocyclization catalyst flowing countercurrent to the gaseous feedstock under conditions effective to convert the methane to higher hydrocarbon(s) and hydrogen in a cascade moving bed reactor system comprising at least first and second series-connected reaction zones. Conveniently, each reaction zone is operated in fluidized bed regime in which the superficial gas velocity exceeds the minimum fluidization velocity ($U_{mf}$) but is less than the velocity required for maintaining a solid bed void fraction below 95 vol. %.

During the methane aromatization reaction, coke tends to build up on the particulate dehydrocyclization catalyst and hence a portion of the particulate dehydrocyclization catalyst may be periodically regenerated in a regeneration zone, which is separate from the reaction zone and is normally operated under oxidizing conditions. Under the oxidizing conditions in the regeneration zone, coke is burnt from the catalyst but at the same time the activity of the catalyst tends to be adversely affected, either by conversion of elemental metal or metal carbides on the catalyst to oxide forms or by generation of coke selective sites on the catalyst. Accordingly, in one embodiment of the present process, the regenerated catalyst is transferred to a catalyst treatment zone separate from the reaction zone and the regeneration zone, where the regenerated catalyst is contacted with a carburizing gas at a temperature less than the temperature in the reaction zone, but generally greater than the temperature in the regeneration zone. The use of the separate catalyst treatment zone allows the contact with the carburizing gas to be conducted under conditions which favor conversion of metal oxides on the regenerated catalyst back to carbide species or the elemental form as well as enhancing the aromatics selectivity of the catalyst. Moreover, any by-products, such as hydrogen, generated as a result of the contact with the carburizing gas can be removed from the catalyst treatment zone without being combined with the effluent from the reaction zone.

The dehydrocyclization reaction is endothermic and the present disclosure also provides a method for supplying heat to the reaction by withdrawing a further portion of the catalyst from the reaction zone, heating the further catalyst portion in a heating zone with hot combustion gases generated by burning a supplemental source of fuel and then returning the heated catalyst portion to the reaction zone. The heated catalyst portion is preferably fed to the catalyst treatment zone for contact with the carburizing gas before being returned to the reaction zone.

In addition, this disclosure provides a process for utilizing the hydrogen generated as a by-product of the dehydrocyclization reaction and in particular to a process for converting at least part of the hydrogen to higher value products.

Feedstock

Any methane-containing feedstock can be used in the process of this disclosure but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbon(s) that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in the hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 parts per million by weight (wtppm), for example less than 10 wtppm, such as less than 1 wtppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol. %, such as about 97 to about 99 mol. %, methane and about 0.1 to about 10 mol. %, such as about 1 to about 3 mol. %, $CO_2$. In additional embodiments, the feed to the dehydrocyclization step contains carbon monoxide and comprises about 80 to about 99.9 mol. %, such as about 94 to about 99 mol. %, methane and about 0.1 to about 20 mol. %, such as about 1 to about 6 mol. %, CO. In a further embodiment, the feed to the dehydrocyclization step contains steam and comprises about 90 to about 99.9 mol. %, such as about 97 to about 99 mol. %, methane and about 0.1 to about 10 mol. %, such as about 1 to about 5 mol. %, steam. In yet a further embodiment, the feed to the dehydrocyclization step contains hydrogen and comprises about 80 to about 99.9 mol. %, such as about 95 to about 99 mol. %, methane and about 0.1 to about 20 mol. %, such as about 1 to about 5 mol. %, hydrogen.

The feed to the dehydrocyclization step can also contain higher hydrocarbon(s) than methane, including aromatic hydrocarbon(s). Such higher hydrocarbon(s) can be recycled from the hydrogen rejection step, added as separate co-feeds or can be present in the methane stream, such as, for example, when ethane is present in a natural gas feed. Higher hydrocarbon(s) recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt. %, such as less than 3 wt. %, of $C_3+$ hydrocarbon(s).

Dehydrocyclization

In the dehydrocyclization step of the present process, the methane containing feedstock is contacted with a dehydrocyclization catalyst under conditions, normally non-oxidizing conditions and preferably reducing conditions, effective to convert the methane to higher hydrocarbon(s), including benzene and naphthalene. The principal net reactions involved are as follows:

$$2CH_4 \leftrightarrow C_2H_4 + 2H_2 \tag{Reaction 1}$$

$$6CH_4 \leftrightarrow C_6H_6 + 9H_2 \tag{Reaction 2}$$

$$10CH_4 \leftrightarrow C_{10}H_8 + 16H_2 \tag{Reaction 3}$$

Carbon monoxide and/or dioxide that may be present in the feed improves catalyst activity and stability by facilitating reactions such as:

$$CO_2 + coke \rightarrow 2CO \tag{Reaction 4}$$

but negatively impacts equilibrium by allowing competing net reactions, such as;

$$CO_2 + CH_4 \leftrightarrow CO + 2H_2 \tag{Reaction 5}.$$

Suitable conditions for the dehydrocyclization step include a temperature of about 400° C. to about 1200° C., such as about 500° C. to about 975° C., for example about 600° C. to about 950° C., a pressure of about 1 kPa-a to about 1000 kPa-a, such as about 10 to about 500 kPa-a, for example about 50 kPa-a to about 200 kPa-a and a weight hourly space velocity of about 0.01 to about 1000 hr$^{-1}$, such as about 0.1 to about 500 hr$^{-1}$, for example about 1 to about 20 hr$^{-1}$. Conveniently, the dehydrocyclization step is conducted in non-oxidizing conditions. Generally, the dehydrocyclization reaction conditions are sufficient to convert at least 5 wt. %, for example 7 wt. %, such as at least 10 wt. %, for example at least 12 wt. %, and such as at least 15 wt. %, of the methane in the feedstock to higher hydrocarbon(s), generally to aromatic hydrocarbon(s), and particularly to benzene.

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in elemental form or as a carbide species.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of suitable catalysts include molybdenum, tungsten, zinc, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements (IUPAC 2005). Such modifications can be used to alter the surface activity of the support and hinder or enhance access to any internal pore structure of the support.

In some embodiments, the catalytic particulate material may further comprise non-catalytic particulate material. The non-catalytic particulate material may be used as a material to transport energy (heat) into the system and/or to fill space as required providing the required hydrodynamic environment. The non-catalytic particulate material may form particulates without binder or be bound by an inorganic binder such as clay, silica, alumina, zirconia, or other metal oxide may be used to help maintain the physical integrity of the particles. Preferably the particles are of a substantially spherical shape. Examples of suitable non-catalytic particulate material are low surface area silica, alumina, ceramics, and silicon carbide.

The dehydrocyclization step is conducted by contacting the methane-containing feedstock with the particulate dehydrocyclization catalyst in a reactor system comprising two or more series-connected moving bed reaction zones. Generally, the feedstock is contacted in each reaction zone with the dehydrocyclization catalyst, wherein the bulk of the feedstock flows countercurrent to the direction of movement of the bulk of the dehydrocyclization catalyst. In some embodiments, the reaction zone comprises a plurality of series-connected moving bed reaction zones in which particulate catalyst is cascaded in one direction from one reaction zone to the next adjacent reaction zone in the series, while the feed is passed through and between the reaction zones in the opposite direction.

In one embodiment, each of the moving bed reaction zones is operated as a fluidizing bed reaction zone, that is with the superficial gas velocity (U) being sufficient to fluidize the solid catalyst and non-catalyst particles. In particular, the superficial gas velocity is above the minimum fluidization velocity $U_{mf}$ of the solid catalyst and non-catalyst particles but below the velocity required for dilute-phase pneumatic conveying of said solid particles in order to maintain a solids bed with void fraction below about 95%. Typically, the superficial gas velocity is maintained from 1.01 times the minimum fluidization velocity ($U_{mf}$) to 0.99 times the velocity required for maintaining a solid bed void fraction below 95 vol. %. The actual numeric value of the superficial velocity will be a function of the average diameter of the particles, the reactor operating temperature, the reactor operating pressure, and the feed composition. For example, for 70 micron particles in a reactor feeding pure methane and operated at 800° C. and 20 psia (138 kPa), the acceptable range of superficial velocities would be from greater than about 1.3 meters per second to less than about 2.3 meters per second. For example for 500 micron particles in a reactor feeding pure methane and operated at 800° C. and 50 psia (345 kPa), the acceptable range of superficial velocities would be from greater than about 4.6 meters per second to less than about 8.5 meters per second. Generally, the superficial gas velocity is greater than 1 meter/second.

In other embodiments, wherein the reaction zones are operated as fluidizing beds, the catalytic particulate material and/or any non-catalytic particulate material has an average particle size from about 0.01 mm to about 10 mm, such as from about 0.05 mm to about 1 mm, and for example from about 0.1 mm to about 0.6 mm. In some embodiments, at least 90 wt. % of the catalytic particulate material and/or at least 90 wt. % of the non-catalytic particulate material have particle size from about 0.01 mm to about 10 mm, such as from about 0.05 mm to about 1 mm, and for example from about 0.1 mm to about 0.6 mm.

In some embodiments, the mass ratio of the flowrate of the catalytic particulate material plus any non-catalytic particulate material over the flowrate of the hydrocarbon feedstock is from about 1:1 to about 100:1, such as from about 5:1 to about 60:1, for example from about 9:1 to 25:1.

In some embodiments, each reaction zone is located in a cold wall reactor. Operation of the metallic shell at lower temperature than the process temperature reduces the cost of the vessel by reducing the required thickness of the vessel wall as well as potentially enabling use of lower cost metal alloy.

Conveniently, the catalytic particulate material enters the reaction zone at a temperature of about 800° C. to about 1200° C. and exits the reaction zone at a temperature of about 500° C. to about 800° C., with the total temperature difference of the catalytic particulate material across the reaction zones being at least −100° C. Generally, the hydrocarbon feed enters the reaction zone at a temperature of about 500° C. to about 800° C. and exits the reaction zone at a temperature of about 750° C. to about 1100° C., with the total temperature difference of the hydrocarbon stream across the reaction zones being at least +100° C. Thus the temperature profile for the reactor system is an inverse temperature profile; that is the reactor system has a hydrocarbon gas inlet reaction temperature lower that the hydrocarbon gas outlet reaction temperature—the inverse of the temperature profile naturally achieved for an endothermic reaction.

The major components of the effluent from the dehydrocyclization step are hydrogen, benzene, naphthalene, carbon monoxide, ethylene, and unreacted methane. Typically, the effluent contains at least 5 wt. %, such as at least 10 wt. %, for example at least 20 wt. %, preferably at least 30 wt. %, more aromatic rings than the feed.

The benzene and naphthalene are then recovered from the dehydrocyclization effluent, for example, by solvent extraction followed by fractionation. However, as will be discussed below, at least part of these aromatic components can be submitted to an alkylation step, before or after product recovery, to produce higher value materials, such as xylenes.

Catalyst Reheating

The dehydrocyclization reaction is endothermic and in order to supply heat to the reaction, a first portion of the catalyst may be withdrawn from the reaction zone, either on an intermittent, or more preferably, a continuous basis, and transferred to a separate heating zone, where the first catalyst portion is heated by direct contact with hot combustion gases generated by burning a supplemental source of fuel. The heated first catalyst portion is then returned to the reaction zones.

Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, the use of an oxygen-lean atmosphere inhibits oxidation of metal carbides present in the dehydrocyclization catalyst and minimizes the average steam partial pressure thereby reducing catalyst hydrothermal aging.

Alternatively, a suitable supplemental fuel source is hydrogen and, in particular, part of the hydrogen generated as a by-product of the aromatization reaction.

Conveniently, said first catalyst portion is contacted directly with the burning source of fuel in the heating zone. Alternatively, the source of fuel is burned in a combustion zone separate from said heating zone and the combustion gases generated in the combustion zone are fed to the heating zone to heat the first catalyst portion.

In one practical embodiment, the heating zone is elongated and the first catalyst portion is passed through the heating zone from an inlet at or adjacent one end of the heating zone to an outlet at or adjacent the other end of the heating zone, with heat being applied to first catalyst portion at a plurality of locations spaced along the length of the heating zone. In this way, the heat input to the first catalyst portion can be distributed along the length of the heating zone thereby minimizing catalyst surface temperatures and internal gradients.

Where the first catalyst portion is heated by direct contact with the burning source of fuel in the heating zone, gradual heating of the catalyst can be achieved by supplying substantially all of the supplemental fuel to the inlet end of the heating zone and then supplying the oxygen-containing gas incrementally to said heating zone at said plurality of spaced locations along the length of heating zone. Alternatively, substantially all of the oxygen-containing gas required to burn said supplemental fuel can be supplied to the inlet end of the heating zone and the supplemental fuel supplied incrementally to the heating zone at said plurality of spaced locations.

Where the first catalyst portion is heated by direct contact with hot combustion gases generated in a separate combustion zone, gradual heating of the catalyst can be achieved by supplying the hot combustion gases to said plurality of spaced locations along the length of heating zone.

In some embodiments, the heating zone is a riser and said first catalyst portion is passed upwardly through the riser during the reheating step. In practice, the heating zone may include a plurality of risers connected in parallel. Alternatively, said heating zone can include a moving bed of said catalyst.

Typically, the first catalyst portion is at a temperature of about 500° C. to about 900° C. on entering the heating zone and is at a temperature of about 800° C. to about 1000° C. on leaving the heating zone. The hot combustion gases are typically at a temperature of less than 1300° C., preferably less than 1100° C., more preferably less than 1000° C., for example at a temperature in the range of about 800° C. to less than 1000° C. Typically, the heating zone will be operated at pressures between 10 and 100 psia (69 and 690 kPa-a), more preferably between 15 and 60 psia (103 and 414 kPa-a). Typically, the average residence time of catalyst particles in the heating zone will be between 0.1 and 100 seconds, more preferably between 1 and 10 seconds.

Prior to being reintroduced into the reaction zone(s) and, preferably after passage through the heating zone, the first catalyst portion may be subjected to one or more stripping steps to at least partially remove (a) coke or heavy hydrocarbon(s) that may have been produced on the surface of the catalyst and/or (b) water or oxygen that may have been adsorbed by the catalyst. Stripping to remove coke or heavy hydrocarbon(s) is conveniently effected by contacting the first catalyst portion with steam, hydrogen and/or $CO_2$, whereas stripping to remove water or oxygen is conveniently effected by contacting the first catalyst portion with methane, $CO_2$ or hydrogen.

In addition, since the reheating step may tend to oxidize catalytically active metal species, particularly metal carbides, contained by the first catalyst portion, the reheated catalyst is preferably subjected to a carburizing step prior to being reintroduced into the reaction zone. Conveniently, the carburization step is effected by contacting the first catalyst portion with $H_2$, and CO, $CO_2$, and/or a hydrocarbon, such as methane, ethane, or propane, and can be conducted simultaneously with or separately from the water/oxygen stripping step. Preferably, carburization of the reheated catalyst is effected in the catalyst treatment zone discussed in detail below.

Catalyst Regeneration

As well as being endothermic, the dehydrocyclization reaction tends to deposit coke on the catalyst and hence, to maintain the activity of the dehydrocyclization catalyst, a second portion of the catalyst may be withdrawn from the reaction zone, either on an intermittent, or a continuous basis, and transferred to a separate regeneration zone. The gas used to transport the second catalyst portion to the regeneration zone may contain $O_2$ but preferably contains less $O_2$ than air, such as less than 10 wt. % $O_2$, most preferably less than 5% $O_2$. The transporting gas may contain $CO_2$ and/or $H_2$ to gasify a portion of the coke from the second catalyst portion, but preferably is substantially free of $H_2O$ and is at a low temperature (typically less than 200° C.) so that the catalyst stream does not oxidize and heat up above the target temperature of the regeneration zone.

The regeneration zone may be a reactor operated as a fluidizing bed, an ebulating bed, a settling bed, a riser reactor or a combination thereof. In practice, the regeneration zone may include a plurality of reactors, such as a plurality of riser reactors connected in parallel. The regeneration zone should be operated at the minimum temperature required to remove the required amount of coke at the design residence time and in particular the temperature should not exceed the point at which metal oxide volatilization occurs or the catalyst substrate undergoes rapid deterioration. Generally, the temperature in the regeneration zone is less than the temperature of the reaction zone and typically regeneration zone temperature is from about 400° C. to about 700° C., such as from about 550° C. to about 650° C. Catalyst residence time in the regeneration zone also should be minimized to reduce catalyst aging rate and maximize percent of time the catalyst spends in the reactor doing useful work. Typically, the average residence time of catalyst particles in the regeneration zone will be between 0.1 and 100 minutes, more preferably between 1 and 20 minutes.

Conveniently, the ratio of the weight of the first catalyst portion transferred in a given time to the heating zone to the weight of second catalyst portion transferred in the same time to the regeneration zone is in the range of about 5:1 to about 100:1, preferably about 10:1 to about 20:1.

In addition to removing coke on the catalyst, the oxygen-containing gas in the regeneration zone tends to react with the metal on the catalyst, thereby converting the metal from the elemental or carbidic species desired for the dehydroaromatization reaction to less active oxide species. Moreover, and particularly where the support is a zeolite, the regeneration step may produce active sites on the surface of the catalyst support that favor coke deposition. Thus, before being returned to the reaction zone, the regenerated catalyst is transferred to a catalyst treatment zone separate from the regeneration zone, the heating zone and the reaction zone, where the regenerated catalyst is contacted with a carburizing gas containing at least one hydrocarbon selected from methane, ethane, propane, butane, isobutene, benzene and naphthalene. In some cases, the carburizing gas may also contain at least one of $CO_2$, CO, $H_2$, $H_2O$ and other diluents. Moreover, it may be desirable to contact the regenerated catalyst sequentially with a plurality of different hydrocarbon(s), each hydrocarbon being selected from methane, ethane, propane, butane, isobutene, benzene and naphthalene.

The catalyst treatment zone may be operated as a fluidizing bed reactor, ebulating bed reactor, settling bed reactor, riser reactor or circulating riser reactor. In one preferred embodiment, the catalyst treatment zone comprises a settling bed reactor. Alternatively, the catalyst treatment zone comprises a single fluidizing bed reactor with internal baffles to prevent back-mixing or a plurality of fluidizing bed reactors in series with the regenerated catalyst being cascaded between adjacent reactors. In any event, contact in the catalyst treatment zone is facilitated by arranging that the regenerated catalyst and the carburizing gas flow in opposite directions in said catalyst treatment zone.

For some catalysts, it may be preferable that the regenerated catalyst portion is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

After leaving the carburization zone, the second catalyst portion is returned to the reaction zone to contact the methane feed. In one practical embodiment, the dehydrocyclization step is conducted in a plurality of fluidizing bed reactors connected in series, with the feedstock entering the first reactor in the series and the heated first catalyst portion and the regenerated second catalyst portion being returned to the final reactor in the series. The hydrocarbon stream and catalyst particulate stream are then conveyed counter current to one another through the series of reactors. Conveniently, said first and second catalyst portions are removed from the first reactor.

In yet a further embodiment, the regeneration or catalyst coke stripping may be effected utilizing hydrogen containing gas. The regeneration conditions when utilizing hydrogen comprise a temperature from about 600° C. to about 1000° C.; such as from about 700° C. to about 950° C., for example from about 800° C. to about 900° C. Generally the hydrogen containing gas should not contain significant quantities of methane or other hydrocarbons; and typically contains less than 20 mol %; such as less than 10 mol %; for example less than 2 mol % hydrocarbon.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, preferably CO and/or $CO_2$, to produce water and a second effluent stream having a reduced hydrogen content compared with the first (dehydrocyclization) effluent stream.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbon(s), in which case, after separation of the co-produced water, at least portion of the hydrocarbon(s) are conveniently recycled to the dehydrocyclization step. For example, where the hydrocarbon(s) produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbon(s) produced in the hydrogen rejection step comprise aromatics, the portion recycled to the dehydrocyclization step conveniently comprises single ring aromatic species.

Methanation/Ethanation

In some embodiments the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 6)}$$

$$2CO_2 + 7H_2 \leftrightarrow C_2H_6 + 4H_2O \quad \text{(Reaction 7)}$$

The carbon dioxide employed is conveniently part of a natural gas stream and preferably the same natural gas stream used as the feed to the dehydrocyclization step. Where the carbon dioxide is part of a methane-containing stream, the $CO_2:CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2:CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa-a to about 20,000 kPa-a, such as about 500 to about 5000 kPa-a and a weight hourly space velocity of about 0.1 to about 10,000 $hr^{-1}$, such as about 1 to about 1,000 $hr^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbon(s). In addition, some partial hydrogenation of the carbon dioxide to carbon monoxide is preferred. After removal of the water, the methane, carbon monoxide, any unreacted carbon dioxide and higher hydrocarbon(s) can be fed directly to the dehydrocyclization step to generate additional aromatic products.

Fischer-Tropsch Process

In additional embodiments the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, preferably about 1.5:1 to about 2.5:1, at a temperature of about 175° C. to about 400° C., preferably about 180° C. to about 240° C. and a pressure of about 1 to about 100 bar (100 to 10,000 kPa-a), preferably about 10 to about 40 bar (1,000 to 4,000 kPa-a), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In some embodiments, the catalyst comprises a non-shifting catalyst, e.g., cobalt or ruthenium, preferably cobalt, with rhenium or zirconium as a promoter, preferably cobalt and rhenium supported on silica or titania, preferably titania.

In additional embodiments, the hydrocarbon synthesis catalyst comprises a metal, such as Cu, Cu/Zn or Cr/Zn, on the ZSM-5 and the process is operated to generate significant quantities of single-ring aromatic hydrocarbon(s). An example of such a process is described in *Study of Physical Mixtures of $Cr_2O_3$—ZnO and ZSM-5 Catalysts for the Transformation of Syngas into Liquid Hydrocarbon(s)* by Jose Erena; Ind. Eng. Chem Res. 1998, 37, 1211-1219, incorporated herein by reference.

The Fischer-Tropsch liquids, i.e., $C_5+$, are recovered and light gases, e.g., unreacted hydrogen and CO, $C_1$ to $C_3$ or $C_4$ and water are separated from the heavier hydrocarbon(s). The heavier hydrocarbon(s) can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \quad \text{(Reaction 8)}$$

and by the following reaction:

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO + CO_2$) in the range of from about 0.5:1 to about 20:1, preferably in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In some embodiments, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa-a to about 12,500 kPa-a, such as from about 2,000 kPa-a to about 10,000 kPa-a, for example 2,500 kPa-a to about 7,500 kPa-a. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, more preferably from about 500 $hr^{-1}$ to about 10,000 $hr^{-1}$. This exothermic reaction may be carried out in either fixed or fluidizing beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet additional embodiments, the hydrogen rejection step comprises selective hydrogen combustion, which is a process in which hydrogen in a mixed stream is reacted with oxygen to form water or steam without substantially reacting hydrocarbon(s) in the stream with oxygen to form carbon monoxide, carbon dioxide, and/or oxygenated hydrocarbon(s). Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a hydrocarbon feedstock comprising hydrocarbon and hydrogen and a catalytic particulate material comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:
  i) at least one metal from Group 3 and at least one metal from Groups 4-15 of the Periodic Table of the Elements;
  ii) at least one metal from Groups 5-15 of the Periodic Table of the Elements, and at least one metal from at least one of Groups 1, 2, and 4 of the Periodic Table of the Elements;
  iii) at least one metal from Groups 1-2, at least one metal from Group 3, and at least one metal from Groups 4-15 of the Periodic Table of the Elements; and
  iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present disclosure is generally conducted at a temperature in the range of from about 300° C. to about 850° C. and a pressure in the range of from about 1 atm to about 20 atm (100 to 2000 kPa-a).

Aromatic Product Recovery/Treatment

The major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin).

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e, those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In some embodiments of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa-a), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa-a), a WHSV based on ethylene of from about 0.1 to about 20 hr$^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In additional embodiments of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa-a). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa-a to about 10,000 kPa-a, such as about 2,000 kPa-a to about 10,000 kPa-a, for example about 3000 kPa-a to about 5,000 kPa-a. Gas hourly space velocities may vary depending upon the type of process used, but generally the gas hourly space velocity of flow of gas through the catalyst bed is in the range of about 50 hr$^{-1}$ to about 50,000 hr$^{-1}$, such as about 250 hr$^{-1}$ to about 25,000 hr$^{-1}$, more preferably about 500 hr$^{-1}$ to about 10,000 hr$^{-1}$.

The effluent from the reverse shift reactor can then be fed to an alkylation reactor operating under conditions to cause reactions such as the following to occur:

$$CO + 2H_2 \leftrightarrow CH_3OH \quad \text{(Reaction 9)}$$

$$CH_3OH + C_6H_6 \rightarrow toluene + H_2O \quad \text{(Reaction 10)}$$

$$2CH_3OH + C_6H_6 \rightarrow xylenes + 2H_2O \quad \text{(Reaction 11)}$$

Suitable conditions for such an alkylation reactor would include a temperature of about 100 to about 700° C., a pressure of about 1 to about 300 atmospheres (100 to 30,000 kPa-a), and a WHSV for the aromatic hydrocarbon of about 0.01 to about 100 hr$^{-1}$. A suitable catalyst would comprise a molecular sieve having a constraint index of 1 to 12, such as ZSM-5, typically together with one or metals or metal oxides, such as copper, chromium and/or zinc oxide.

Preferably, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, and preferably a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa-a), such as about 100 to about 500 psig (790 to 3550 kPa-a) and a WHSV of about 0.5 to about 50 $hr^{-1}$, such as about 2 to about 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa-a), such as about 100 to about 500 psig (790 to 3550 kPa-a) and a WHSV of about 0.5 to about 50 $hr^{-1}$, such as about 2 to about 10 $hr^{-1}$.

This disclosure will now be more particularly described with reference to the accompanying drawing and the following non-limiting Examples.

Referring to FIG. 1, the drawing illustrates a simplified design of a dehydrocyclization reactor system for converting methane to aromatics according to one embodiment of the invention. In this embodiment, the dehydrocyclization reactor includes two series-connected moving bed reactors, 11 and 12, in which particulate catalyst is cascaded in one direction from one reactor to the next adjacent reactor in the series, while the feed is passed through and between the reactors in the opposite direction. The heated catalyst flows through an inlet located adjacent the top of the reactor 11 via line 13 and from which cooled catalyst flows via outlet 14 located adjacent the base of the reactor 11 into the reactor 12 via inlet 15. The catalyst flows out of reactor 12 via an outlet adjacent the base of the reactor 12 via line 16. Methane feed 17 is introduced into the reactor 12 adjacent the base thereof via line 17. The product and unreacted methane flows out of reactor 12 through an outlet adjacent to the top of reactor 12 via outlet 18 and feeds to reactor 11 via an inlet adjacent to the base of thereof via line 18. The final product is removed from reactor 11 through an outlet adjacent to the top of the reactor 11 via line 20. Typically, the heated catalyst enters the reactor 11 at a temperature of about 850° C. and the cooled catalyst leaves the reactor at a temperature of about 600° C. FIG. 1 portrays the zones being in separate vessels however the two zones may be located in a single vessel with appropriate internals to maintain the two zones. One having ordinary skill in the art understands that the reactor system may contain more than two cascade moving beds, e.g., 3, 4, or 5 series-connected moving beds reactors or zones.

One having ordinary skill in the art understands that the embodiments discussed in this application do not represent all the possible apparatus or process variations embodied by the present disclosure. In addition, many pieces of equipment and apparatus and certain processing steps may be needed for industrial, commercial or even experimental purposes. Examples of such equipments and apparatus and processing steps are, but not limited to, distillation columns, fractionation columns, heat exchanges, pumps, valves, pressure gauges, temperature gauges, liquid-vapor separators, feed and product driers and/or treaters, clay treaters, feed and/or product storage facilities, and processes and steps for process control. While such equipment, apparatus and steps that are not needed for understanding the essence of the present disclosure are not shown in the drawings, some of them may be mentioned from time to time to illustrate various aspects of the invention. It is also noted that some of the equipment may be placed at different places in the process depending on the conditions of the processes.

The following examples are intended to illustrate the two key benefits of the present process:
  (a) Improved product selectivity: Reduced production of coke and increased production of high value products (benzene, toluene, and naphthalene). Reduction in coke selectivity has two fold benefits: improved feed utilization and reduction in deactivation rate of the catalyst.
  (b) Reduced catalyst circulation rates which will reduce the attrition rate of the catalyst as well as reduce the erosion rate of reaction vessels, reactor internals, transfer lines, and other associated equipments.

EXAMPLE 1

Mo/ZSM-5 catalysts were prepared via impregnation of ammonium heptamolybdate solution onto an $NH_4ZSM-5$ support (having a $Si/Al_2$ ratio of 28) via incipient wetness, followed by drying at 120° C. for 2 hours and final calcination at 500° C. for 6 hours in flowing air. A nominal molybdenum loading of 2.7 wt. % (wt. % of metal based on the total weight of the catalyst) was targeted; although minor variations in molybdenum loadings do not affect the conclusions obtained. Each Mo/ZSM-5 catalyst sample (after calcination) was pelletized, crushed and sieved to 30-60 mesh particle size. Catalytic testing of the Mo/ZSM-5 catalysts was performed in a quartz reactor packed to form a fixed-bed using quartz wool supports.

Catalyst performance for methane dehydrocyclization to benzene was performed at various temperatures using a 95 wt. % $CH_4$-5 wt. % argon feed (argon is used as internal standard) at a weight-hourly space velocity (based on methane) of 1.2 $hr^{-1}$. All experimental data were obtained at 138 kPa-a (20 psia) and all modeling was also performed at the same pressure. The reaction effluent was analyzed using a mass spectrometer and gas chromatograph to determine the methane, benzene, toluene, ethylene, naphthalene, hydrogen, and argon concentrations. The rate of coke deposition on the catalyst (i.e., heavy carbonaceous deposit which does not volatize from catalyst surface) was determined via carbon balance. Additional data were obtained at two temperatures (750° C. and 800° C.) with $H_2$ added to the feed at 6 mol % and 20 mol % respectively. For the purposes of these examples the experimental data were consolidated to two values $Sel_{BTN}$ and $Sel_{Coke}$. The $Sel_{BTN}$ is the average selectivity on a carbon molar basis as defined by the sum of the moles of carbon in the product present in benzene, toluene, and naphthalene divided by the moles of carbon contained in methane that reacted. The $Sel_{Coke}$ is the average selectivity on a carbon molar basis as defined by the sum of the moles of carbon that remains in the reactor divided by the moles of carbon contained in methane that reacted. The sum of $Sel_{BTN}$ and $Sel_{Coke}$ does not equal to 100% due to the formation of other minor products, predominately ethylene. As it is often difficult to obtain accurate experimental thermodynamic conversion data, commercially available simulation software (PROII/6.0 Copyright 2003 Invensys Systems Inc.) was utilized to establish the value $Conv_{BL}$. The $Conv_{BL}$ is defined as the maximum thermodynamically obtainable conversion of methane to benzene and hydrogen (i.e the reaction set was constrained to just the reaction of methane to benzene plus hydrogen so that there were no other products such as coke, naphthalene, ethylene, etc) at a given temperature and 138 kPa-a (20 psia) pressure. The experimental and modeling results are shown in Table 1.

TABLE 1

| Temp ° C. | $H_2$ Co-Feed Mol % | $Sel_{BTN}$ | $Sel_{Coke}$ % C onFeed | $Conv_{BL}$ |
|---|---|---|---|---|
| 600 | 0% | 99% | 0.01% | 5% |
| 650 | 0% | 98% | 0.1% | 8% |
| 700 | 0% | 96% | 1% | 12% |
| 750 | 0% | 85% | 9% | 17% |
| 750 | 6% | 89% | 5% | |
| 800 | 0% | 68% | 24% | 23% |
| 800 | 20% | 84% | 8% | |
| 850 | 0% | 45% | 46% | 29% |
| 900 | 0% | 20% | 71% | 37% |

It is understood that different catalyst compositions, the use of co-feeds ($CO_2$, CO, $H_2O$, $H_2$, $O_2$, ethane, propane, etc), different operating pressures, and/or different space velocities may change the selectivity and conversion numbers but that, while the exact level of improvement demonstrated by the present process may change, the directional improvements obtained by the process will still be achieved. In addition, it is to be appreciated that, as a basis for the modeling calculations discussed below, it is assumed that the methane feed to the reactor was always preheated to the same temperature (600° C.) and in all cases a nominal feed rate of methane of 100 kilograms per hour was used. It was also used as a basis that the catalyst supplied to the moving bed reactor systems was maintained at the same temperature (850° C.). The quantity of catalyst required to maintain this temperature was calculated for each reactor configuration; that is the quantity of catalyst was calculated such that the hot catalyst provided 100% of the energy required to heat the feed from 600° C. to 800° C. as well as provide 100% of the energy required for the endothermic reactions. For simplicity, it is assumed that the catalyst thermal conductivity, thermal diffusivity and surface emissivity remain constant. The following Table 2 lists the physical constants and catalyst properties used in the calculations.

TABLE 2

| Model Parameters | |
|---|---|
| Catalyst Particle Density | 1400 kg/m$^3$ |
| Catalyst Heat Capacity | 1262 J/kg-K |
| Catalyst Thermal Conductivity | 0.4 W/m-K |
| Catalyst Thermal Diffusivity | 2.26 × 10$^{-7}$ m$^2$/s |
| Catalyst Surface Emissivity | 0.85 |

To allow modeling of various reactor configurations, equations were obtained for $Sel_{BTN}$, $Sel_{Coke}$, and $Conv_{BL}$ by obtaining best fit polynomial equations for the above set of data points; the data points where $H_2$ was included in the feed were not included in the calculations of the equations. The equations obtained and the $R^2$ values are shown below:

$Sel_{BTN}$=(1.81818181818345E−10)T$^4$−
(5.41010101010501E−07)T$^3$+
(5.88000000000377E−04)T$^2$−
(2.78591414141575E−01)T+
4.97583333333585E+01

$R^2_{BTN}$=9.99810335105254E−01  $Sel_{Coke}$=(−
1.85878787878687E−10)T$^4$+
(5.62280808080511E−07)T$^3$−
(6.21721666666349E−04)T$^2$+
(2.99664027416883E−01)T−
5.33408809523590E+01

$R^2_{Coke}$=9.99958406639717E−01  $Conv_{BL}$=
(1.91428571428569E−06)T$^2$−
(1.81714285714283E−03)T+
4.53357142857135E−01

$R^2_{BL}$=9.99955208049633E−01 where T is temperature in degrees C.,

In all examples $R^2$ is the coefficient of determination which compares estimated and actual y-values, and ranges in value from 0 to 1. If it is 1, there is a perfect correlation in the sample—there is no difference between the estimated y-value and the actual y-value. At the other extreme, if the coefficient of determination is 0, the regression equation is not helpful in predicting a y-value. The version used here is based on an analysis of variance decomposition as follows:

$$R^2 = \frac{SS_R}{SS_T} = 1 - \frac{SS_E}{SS_T}.$$

In the above definition, $$SS_T = \sum_i (y_i - \bar{y})^2, SS_R = \sum_i (\hat{y}_i - \bar{y})^2,$$

$$SS_E = \sum_i (y_i - \hat{y}_i)^2.$$

That is, $SS_T$ is the total sum of squares, $SS_R$ is the regression sum of squares, and $SS_E$ is the sum of squared errors.

$R^2_{BTN}$ is coefficient of determination for the $Sel_{BTN}$ correlation, $R^2_{Coke}$ is coefficient of determination for the $Sel_{Coke}$ correlation, and $R^2_{BL}$ is coefficient of determination for the $Conv_{BL}$ correlation.

These set of equations was used to calculate the yields that would be obtained for various reactor configurations where $Yield_{BTN}$ was defined as $Sel_{BTN} \times Conv_{BL}$ integrated over the temperature profile in the reactor system and $Yield_{Coke}$ was defined as $Sel_{Coke} \times Conv_{BL}$ integrated over the temperature profile in the reactor system. While it is recognized and shown in the Table 1, that the byproduct $H_2$ improved the reaction selectivity for the inventive cases, these equations omitted the selectivity improvement so that they provided a conservative estimate as to the level of improvement that the present process would provide.

Transport or Riser Reactor (Comparative)

Utilizing the above equations for a transport or riser reactor with adiabatic declining temperature with an inlet temperature of 850° C. the required catalyst circulation rate to maintain an outlet temperature of 800° C. was 3211 kilograms per hour (kg/hr) based on the nominal feed rate of methane of 100 kg/hr at 600° C. The following yields and selectivities were calculated:

$Sel_{BTN}$=51%
$Sel_{Coke}$=40%
$Yield_{BTN}$=12%
$Yield_{Coke}$=8.9%
$\Delta T_{Reaction}$=−50° C. (negative 50° C.);
$\Delta T_{Catalyst}$=−50° C. (negative 50° C.);

wherein $\Delta T_{Reaction}$ is defined as the product outlet reaction temperature (i.e., the last temperature at which catalytic reaction occurs before the hydrocarbon product leaves the reactor system) minus the hydrocarbon feed inlet reaction temperature (i.e., the first temperature at which catalytic reaction occurs when the hydrocarbon feed enters the reactor system); and wherein $\Delta T_{Catalyst}$ is defined as the temperature of the supplied catalyst minus the temperature of the exiting catalyst Fixed Bed Reactor (Comparative)

Performing modeling of the potential fixed bed comparative Example resulted in even poorer performance than with the transport or riser reactor because in the fixed bed configuration the entire heat of reaction had to be supplied by the methane containing stream (since no moving catalyst was used to supply heat to the reaction zone). Therefore, the fixed bed reactor required that the methane containing stream had to be heated to a temperature much greater than the desired outlet temperature of 800° C., thereby resulting in a larger magnitude $\Delta T$; that is a $\Delta T$ of −60° C. or more negative.

Cascaded Fluid Beds (2 Fluidized Beds)

Similar to what is shown in FIG. 1; this Example is for 2 cascaded fluid beds. By cascaded fluid beds it is meant that there are 2 or more reaction stages or zones operating at different temperatures with particulate catalyst moving from one stage to the next and hydrocarbon gas moving from one stage to the next in the direction opposite that of the catalyst movement. In the case simulated for two cascaded fluidized beds of catalyst, the first bed was operated at 731 ° C. and the second bed was operated at 800° C.; the required catalyst circulation rate was reduced to 1367 kg/hr and the reaction results were improved:

$Sel_{BTN}$=81%
$Sel_{Coke}$=13%
$Yield_{BTN}$=18%
$Yield_{Coke}$=2.8%
$\Delta T_{Reaction}$=+69° C.
$\Delta T_{Catalyst}$=−119° C. (negative 119° C.).

Cascaded Fluid Beds (3 Fluidized Beds)

In the case simulated for three cascaded fluidized beds of catalyst, the first bed was operated at 690° C., the second bed was operated at 753° C. and the third bed was operated at 800° C., the catalyst circulation rate was reduced to 1020 kg/hr and the reaction results were improved:

$Sel_{BTN}$=85%
$Sel_{Coke}$=10%
$Yield_{BTN}$=19%
$Yield_{Coke}$=2.2%
$\Delta T_{Reaction}$=+110° C.
$\Delta T_{Catalyst}$=−160° C. (negative 160° C.).

Cascaded Fluid Beds (4 Fluidized Beds)

In the case simulated for four cascaded fluidized beds of catalyst, the first bed was operated at 669° C., the second bed was operated at 723° C., the third bed was operated at 762° C., and the fourth bed was operated at 800° C., the catalyst circulation rate was reduced to 900 kg/hr and the reaction results were improved:

$Sel_{BTN}$=86%
$Sel_{Coke}$=9%
$Yield_{BTN}$=19%
$Yield_{Coke}$=2.0%
$\Delta T_{Reaction}$=+131° C.
$\Delta T_{Catalyst}$=−181° C. (negative 181° C.).

Cascaded Fluid Beds (5 Fluidized Beds)

In the case simulated for five cascaded fluidized beds of catalyst, the first bed was operated at 655° C., the second bed was operate at 703° C., the third bed was operated at 737° C., the fourth bed was operated at 767° C., and the fifth bed was operated at 800° C., the catalyst circulation rate was reduced to 838 kg/hr and the reaction results were improved:

$Sel_{BTN}$=87%
$Sel_{Coke}$=8%
$Yield_{BTN}$=20%
$Yield_{Coke}$=1.8%
$\Delta T$ =+145° C.
$\Delta T_{Catalyst}$=−195° C. (negative 195° C.).

As illustrated by the above examples, more reaction zones achieve better results, although it will be appreciated that the reaction system investment will increase with increasing number of zones (or stages). There is optimum number of zones (or stages) which depends on the economic of the process.

EXAMPLE 2

Based on the model predicted advantages for an inverse temperature profile, a laboratory scale unit was constructed to validate the model results. While the model was oriented toward operation of the reaction system as a cascaded fluid bed, the laboratory reactor was a fixed bed of catalyst with an inverse temperature profile imposed by use of external heaters. In all cases the experimentally observed conversions fell below the model predicted conversions. This may be due to laboratory scale experimental artifacts such as bed bypassing and or/back mixing due to the hydrodynamic regime in which the lab scale reactors operate.

Mo/ZSM-5 catalyst was prepared via ball milling of 7.5 wt % Mo (wt % of metal based on the total weight of the catalyst) as $MoO_3$ with $NH_4ZSM$-5 support (having a $Si/Al_2$ ratio of 25) for 2 hr, followed by calcination at 500° C. for 5 hr in air. The catalyst was pelletized, crushed, and sieved to 20-40 mesh particle size. Catalytic testing of the Mo/ZSM-5 catalyst was performed in a fixed bed quartz reactor with an inner diameter of 7 mm and a bed length of about 18 cm. Inert quartz particles (20-50 mesh) were used as a bed diluent so that all beds were the same length.

Catalyst performance for methane dehydrocyclization to benzene was performed using a 95 vol % $CH_4$/5 vol % Ar feed (argon was used as an internal standard). All experimental reaction data was obtained at 20 psia (138 kPa-a). The reaction effluent was analyzed using a mass spectrometer to determine product concentrations.

Ten separate catalyst performance experiments were conducted for comparison. In all experiments the catalyst was activated by heating in 15 vol % $CH_4$/80 vol % $H_2$/5 vol % Ar at 5° C./min to 800° C. and holding for 30 min. This was followed by aging the catalyst with 5 cycles of reaction and regeneration (also identical for all ten experiments). Each reaction segment lasted 20 minutes at 800° C. in 95 vol % $CH_4$/5 vol % Ar feed at 1.4 $hr^{-1}$ weight-hourly space velocity (WHSV) based on $CH_4$. Each regeneration segment consisted of switching to $H_2$, heating to 850° C. with a 10 min. hold time, then cooling back to 800° C. (total time on $H_2$ of 14 min.). The ten experiments differed only on their sixth reaction cycle which was run in 95 vol % $CH_4$/5 vol % Ar feed for 4 hours. Conditions for the sixth cycle were selected to compare the effects of catalyst bed temperature profile at different space velocities. In particular, experiments 1 to 5 were run at WHSV values varying between 0.25 and 8 $hr^{-1}$ with bed being held at isothermal conditions at 800° C. In contrast, experiments 6 to 10 were run over the same range of WHSV values but with a linear gradient in bed temperature of 650° C. at the feed inlet to 800° C. at the product outlet (inverse temperature profile). Table 3 summarizes the catalyst performance results for the ten experiments during reaction cycle #6.

The results in Table 3 show that there was a clear advantage for operating with an inverse temperature profile which improved instantaneous selectivity at most space velocities for shorter operation times and consistently acted to prolong selectivity to benzene over longer operation times. This allowed for greater cumulative production in comparison to an isothermal bed at all space velocities.

b) achieving inverse profile by utilizing a series of moving bed reactors with catalyst moving downward with hot catalyst introduced at top of reactor series and reduced temperature catalyst removed from bottom of reactor series. Feed is introduced at bottom of reactor series and flows countercurrent to catalyst up the reactor series so that it contacts the hottest portion of the catalyst at the process gas outlet.

Other advantages of the present process include:

(a) extending catalyst life by minimizing catalyst exposure to high temperature for a given process outlet temperature due to the inversed temperature profile, that is the reactor system has a hydrocarbon gas inlet reaction temperature lower that the hydrocarbon gas outlet reaction temperature—inverse of the temperature profile one would naturally achieve for an endothermic reaction;

(b) maximizing selectivity and/or conversion due to the inversed temperature profile;

(c) providing operating flexibilities, such as more reactive species ($C_2$+) in feed, without substantially increasing in coke formation because of the inversed temperature profile, which allows the feed to contact the cooler/coked catalyst first;

(d) enabling the hottest catalyst to be maintained in a more hydrogen rich environment, which reduces coking rate on the hot and/or freshly regenerated catalyst;

(e) minimizing feed preheat requirements and coking on heat transfer surfaces by providing greater than 50%; preferable about 100% of the heat required for heating the process gas from reactor inlet temperatures to outlet temperatures and the heat required for the endothermic reactions by direct contacting the process gas with hot catalyst;

(f) mitigating metallurgy issues;

(g) adding catalyst continuously to offset catalyst aging;

TABLE 3

| Exp. # | WHSV ($hr^{-1}$) for cycle 6 | Methane conversion (%) at 1 hr | Benzene yield (%) at 1 hr | Benzene selectivity (%) at 1 hr | Methane conversion (%) at 4 hr | Benzene yield (%) at 4 hr | Benzene selectivity (%) at 4 hr | Total Benzene Produced (g $C_6H_6$/g Catalyst) | Increase in Total Benzene Produced |
|---|---|---|---|---|---|---|---|---|---|
| 1 | 0.25 | 17.4 | 10.3 | 60 | 12.5 | 4.5 | 36 | 0.06 | Base |
| 2 | 0.5 | 17.9 | 12.1 | 68 | 5.6 | 0.6 | 11 | 0.15 | Base |
| 3 | 1 | 17.4 | 11.9 | 68 | 1.1 | 0.0 | 0 | 0.24 | Base |
| 4 | 2 | 15.1 | 9.6 | 64 | 0.0 | 0.0 | 0 | 0.36 | Base |
| 5 | 8 | 2.0 | 0.4 | 20 | 0.0 | 0.0 | 0 | 0.38 | Base |
| 6 | 0.25 | 16.2 | 10.0 | 62 | 13.2 | 8.4 | 64 | 0.09 | 50% |
| 7 | 0.5 | 16.5 | 11.0 | 67 | 12.6 | 8.3 | 65 | 0.20 | 33% |
| 8 | 1 | 15.5 | 11.0 | 71 | 9.8 | 6.4 | 65 | 0.35 | 46% |
| 9 | 2 | 12.2 | 8.2 | 67 | 3.8 | 2.3 | 60 | 0.44 | 33% |
| 10 | 8 | 3.9 | 2.6 | 67 | 0.5 | 0.4 | 67 | 0.72 | 90% |

As illustrated by the examples; the present process enables the conversion of methane to higher hydrocarbons, e.g., aromatic compounds, at reduced aging/mechanical-attrition catalyst losses, improved operability, and higher selectivity; i.e., lower coke make; than previously proposed processes, by (a) performing reaction in a series of reaction zones with an inverse temperature profile; that is a reactor system with a process inlet reaction temperature lower that the process gas outlet reaction temperature—inverse of the temperature profile one would naturally achieve for an endothermic reaction; and (h) improving energy efficiency (like a counter current heat exchanger) by reducing catalyst circulation requirements thereby reducing size of associated hardware and catalyst attrition; and/or (i) minimizing product entertainment with exiting catalyst.

While the illustrative embodiments of this disclosure have been described with particularity, it will be understood that various other modifications will be apparent to and can be readily made by those skilled in the art without departing from the spirit and scope of this invention. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which this disclosure pertains.

We claim:

1. A process for converting methane to higher hydrocarbon(s) including aromatic hydrocarbon(s) in a reactor system comprising at least first and second reaction zones connected in series, the process comprising:
   (a) providing to said reactor system a hydrocarbon feedstock containing methane;
   (b) providing to said reactor system a catalytic particulate material;
   (c) moving the bulk of said catalytic particulate material from said first reaction zone to said second reaction zone and moving the bulk of said hydrocarbon feedstock from said second reaction zone to said first reaction zone in the direction opposite that of said catalytic particulate material movement;
   (d) maintaining said reaction zones in a moving bed fashion; and
   (e) operating each of said reaction zones under reaction conditions sufficient to convert at least a portion of said methane to a first effluent comprising said higher hydrocarbon(s);
   further characterized in that the catalytic particulate material enters the reaction zone at a temperature of about 800° C. to about 1200° C. and exits the reaction zone at a temperature of about 500° C. to about 800° C., with the total temperature difference of the catalytic particulate material across the reaction zones being at least −100° C.

2. The process recited in claim 1, wherein said reactor system comprises at least one further reaction zone connected in series with said first and second reaction zones.

3. The process recited in claim 1, and further comprising separating unreacted methane from said first effluent and recycling said unreacted methane to said reaction zones.

4. The process recited in claim 1, wherein said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent.

5. The process recited in claim 4, and further comprising recycling said second effluent to (a).

6. The process recited in claim 1, wherein said reaction zones are operated at a superficial gas velocity of at least 1.01 times the minimum fluidization velocity ($U_{mf}$).

7. The process recited in claim 1, wherein said reaction zones are operated at a superficial gas velocity of less than the velocity required for maintaining a solid bed void fraction below 95 vol. %.

8. The process recited in claim 1, wherein (a) further comprises supplying to said reactor system a non-catalytic particulate material.

9. The process recited in claim 8, wherein the mass ratio of the total flowrate of said particulate material (catalytic particulate material plus any non-catalytic particulate material) to the flowrate of said hydrocarbon feedstock is from about 1:1 to about 100:1.

10. The process recited in claim 1, wherein said reactor zones are contained within one or more cold wall reactors.

11. The process recited in claim 1, wherein said reaction conditions of each reaction zone are non-oxidizing conditions.

12. The process recited in claim 1, wherein said reaction conditions of each reaction zone include a temperature of about 400° C. to about 1200° C., a pressure of about 1 kPa-a to about 1000 kPa-a, and a weight hourly space velocity of about 0.01 $hr^{-1}$ to about 1000 $hr^{-1}$.

13. The process recited in claim 1, wherein said reaction conditions of each reaction zone are sufficient to convert at least a total of 5 wt. % of said methane to said aromatic hydrocarbon(s) across the combined reaction zones.

14. The process recited in claim 1, wherein said catalytic particulate material comprises a metal or compound thereof on an inorganic support, wherein said catalytic particulate material comprises at least one of molybdenum, tungsten, rhenium, a molybdenum compound, a tungsten compound, a zinc compound, and a rhenium compound on ZSM-5, silica or an aluminum oxide.

15. The process recited in claim 1, wherein said hydrocarbon feedstock further comprises at least one of $CO_2$, CO, $H_2$, $H_2O$, or $C_2$+ hydrocarbon(s).

16. The process recited in claim 1, further comprising:
   (f) removing at least a portion of said catalytic particulate material from said reactor system; and
   (g) regenerating at least a portion of the removed catalytic particulate material under regenerating conditions; and
   (h) recycling at least a portion of the regenerated catalytic particulate material to said reactor system.

17. The process recited in claim 16, wherein said regeneration conditions comprise a temperature from about 400° C. to about 750° C. and a regeneration gas comprising oxygen.

18. The process recited in claim 17, wherein said regeneration gas further contains carbon dioxide and/or nitrogen such that the oxygen concentration of said regeneration gas is from about 2 wt. % to about 10 wt. %.

19. The process recited in claim 16, wherein said regeneration conditions comprise a temperature from about 800° C. to about 1200° C. and a regeneration gas comprising hydrogen.

20. The process recited in claim 1, further comprising:
   (f) removing at least a portion of said catalytic particulate material from said reactor system;
   (g) heating at least a portion of the removed catalytic particulate material to a temperature at least 825° C.; and
   (h) recycling at least a portion of the heated catalytic particulate material to said reactor system.

21. The process recited in claim 1, wherein said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent.

22. A process for converting methane to higher hydrocarbon(s) including aromatic hydrocarbon(s) in a reactor system comprising at least first and second reaction zones connected in series, the process comprising:
   (a) providing to said reactor system a hydrocarbon feedstock containing methane;
   (b) providing to said reactor system a catalytic particulate material; wherein said catalytic particulate material provides greater than 50% of the heat required for (e);
   (c) moving the bulk of said catalytic particulate material from said first reaction zone to said second reaction zone and moving the bulk of said hydrocarbon feedstock from said second reaction zone to said first reaction zone;

(d) maintaining said reaction zones in a moving bed fashion; and (e) operating each said reaction zone under reaction conditions sufficient to convert at least a portion of said methane to a first effluent having said higher hydrocarbon(s);

further characterized in that the catalytic particulate material enters the reaction zone at a temperature of about 800° C. to about 1200° C. and exits the reaction zone at a temperature of about 500° C. to about 800° C., with the total temperature difference of the catalytic particulate material across the reaction zones being at least −100° C.

23. The process recited in claim 22, wherein said reactor system comprises at least one further reaction zone connected in series with said first and second reaction zones.

24. The process recited in claim 22, and further comprising separating unreacted methane from said first effluent and recycling said unreacted methane to said reaction zones.

25. The process recited in claim 22, wherein said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent.

26. The process recited in claim 22, wherein said reaction zones are operated at a superficial gas velocity of at least 1.01 times of the minimum fluidization velocity ($U_{mf}$).

27. The process recited in claim 22, wherein said reaction zones are operated at a superficial gas velocity of less than the velocity required for maintaining a solid bed void fraction below 95 vol. %.

28. The process recited in claim 22, wherein said catalytic particulate material comprises at least one of molybdenum, tungsten, rhenium, a molybdenum compound, a tungsten compound, a zinc compound, and a rhenium compound on ZSM-5, silica or an aluminum oxide.

29. A process for converting methane to higher hydrocarbon(s) including aromatic hydrocarbon(s) in a reactor system comprising at least first and second reaction zones connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone;

(d) maintaining said reaction zones in a moving bed fashion;

(e) maintaining said reaction zones with a superficial gas velocity in the range from the minimum fluidization velocity ($U_{mf}$) to the velocity required for maintaining a solid bed void fraction below 95 vol. %;

(f) operating each of said reaction zones under reaction conditions sufficient to convert at least a portion of said methane to a first effluent having said higher hydrocarbon(s);

(g) removing at least a portion of said catalytic particulate material from said reaction zone(s);

(h) regenerating at least a portion of the removed catalytic particulate material under regenerating conditions including a temperature of from about 450° C. to about 750° C.;

(i) heating at least a portion of the removed catalytic particulate material and/or at least a portion of the regenerated catalytic particulate material to a temperature at least 825° C.; and (j) recycling at least a portion of the heated catalytic particulate material to said reaction zones; further characterized in that the catalytic particulate material enters the reaction zone at a temperature of about 800° C. to about 1200° C. and exits the reaction zone at a temperature of about 500° C. to about 800° C., with the total temperature difference of the catalytic particulate material across the reaction zones being at least −100° C.

30. The process recited in claim 29, wherein said reactor system comprises at least one further reaction zone connected in series with said first and second reaction zones.

31. The process recited in claim 29, and further comprising separating unreacted methane from said first effluent and recycling said unreacted methane to said reaction zones.

32. The process recited in claim 29, wherein said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent.

33. The process recited in claim 29, wherein said catalytic particulate material comprises at least one of molybdenum, tungsten, rhenium, a molybdenum compound, a tungsten compound, a zinc compound, and a rhenium compound on ZSM-5, silica or an aluminum oxide.

34. The process recited in claim 29, wherein said superficial gas velocity is maintained from 1.01 times the minimum fluidization velocity ($U_{mf}$) to 0.99 times the velocity required for maintaining a solid bed void fraction below 95 vol. %.

35. The process recited in claim 29, wherein said superficial gas velocity is maintained at greater than 1 meter/second.

36. The process recited in claim 29, wherein (b) further comprises supplying to said reactor system a non-catalytic particulate material.

37. The process recited in claim 36, wherein the mass ratio of the total flowrate of said particulate material (catalytic particulate material plus any non-catalytic particulate material) to the flowrate of said hydrocarbon feedstock is from about 5:1 to about 25:1.

38. The process recited in claim 29, wherein said reaction conditions of each reaction zone include a temperature of about 400° C. to about 1200° C., a pressure of about 1 kPa-a to about 1000 kPa-a, and a weight hourly space velocity of about 0.01 hr$^{-1}$ to about 1000 hr$^{-1}$.

39. A process for manufacturing aromatic hydrocarbon(s) from methane in a reactor system comprising at least first and second reaction zones connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone, wherein said catalytic particulate material enters said second reaction zone at a temperature of about 800° C. to about 1200° C. and exits said second reaction zone at a temperature of about 600° C. to about 800° C. with the total temperature difference of the catalytic particulate material across the reaction zone being at least −100° C.;

(d) maintaining said reaction zones with a superficial gas velocity within a range from the minimum fluidization velocity ($U_{mf}$) to the velocity required for maintaining a solid bed void fraction below 95 vol. %;

(e) operating each said reaction zone under reaction conditions sufficient to convert at least a portion of said methane to a first effluent having said aromatic hydrocarbon(s); and (f) recovering said aromatic hydrocarbon(s).

40. The process recited in claim 39, wherein said reactor system comprises at least one further reaction zone connected in series with said first and second reaction zones.

41. The process recited in claim 39, and further comprising separating unreacted methane from said first effluent and recycling said unreacted methane to said reaction zones.

42. The process recited in claim 39, wherein said range is maintained from 1.01 times of the minimum fluidization velocity ($U_{mf}$) to 0.99 times of the velocity required for maintaining a solid bed void fraction below 95 vol. %.

43. The process of claim 39, and further comprising contacting at least a portion of said aromatic hydrocarbon(s) with a feed containing hydrogen to produce a product having saturates and/or single ring aromatic hydrocarbon(s).

44. The process of claim 39, and further comprising contacting at least a portion of said aromatic hydrocarbon(s) with an alkylating agent to produce a product having xylene(s), ethylbenzene, cumene, or toluene.

45. The process recited in claim 39, wherein said first effluent comprises hydrogen and the process further comprises (i) separating at least part of said hydrogen from said first effluent or (ii) reacting at least part of said hydrogen from said first effluent with oxygen-containing specie(s) to produce a second effluent having a reduced hydrogen content compared with said first effluent.

46. The process recited in claim 45 further comprising a step of recycling said second effluent to step (a).

47. A process for manufacturing benzene from methane in a reactor system having at least a first reaction zone and a final reaction zone connected in series, the process comprising:

(a) providing to said reactor system a hydrocarbon feedstock containing methane;

(b) providing to said reactor system a catalytic particulate material;

(c) moving the bulk of said catalytic particulate material from said first reaction zone to said second reaction zone and moving the bulk of said hydrocarbon feedstock from said second reaction zone to said first reaction zone and wherein the mass ratio of the flowrate of the catalytic particulate material over the flowrate of the hydrocarbon feedstock is from about 1:1 to about 100:1;

(d) maintaining said reaction zones with a superficial gas velocity with a range from the minimum fluidization velocity ($U_{mf}$) to the velocity required for maintaining a solid bed void fraction below 95 vol. %;

(e) operating each said reaction zone under reaction conditions sufficient to convert at least a portion of said methane to said benzene; and (f) recovering said benzene;

further characterized in that the catalytic particulate material enters the reaction zone at a temperature of about 800° C. to about 1200° C. and exits the reaction zone at a temperature of about 500° C. to about 800° C., with the total temperature difference of the catalytic particulate material across the reaction zones being at least −100° C.

48. The process recited in claim 47, wherein said reactor system comprises at least one further reaction zone connected in series between said first and final reaction zones.

49. The process recited in claim 47, further comprising steps of separating unreacted methane from said benzene and recycling said unreacted methane to said reaction zones.

50. The process recited in claim 47, wherein the reactor system includes a catalyst engaging portion, where said hydrocarbon feedstock first contacts said catalytic particulate material in said first reaction zone and a catalyst disengaging portion, where said first effluent disengages from contact with said catalytic particulate material in said final reaction zone, and wherein the temperature profile of said reactor system is maintained such that the difference between the temperature of said first effluent at the catalyst disengaging portion and the temperature of said hydrocarbon feedstock at the catalyst engaging portion is at least +10° C.

* * * * *